United States Patent [19]

Diaz et al.

[11] 4,337,194
[45] Jun. 29, 1982

[54] PROCESS FOR THE PREPARATION OF SOMATOSTATIN

[75] Inventors: Joseph Diaz, Perols; Remy Guegan, Castelnau le Lez, both of France

[73] Assignee: C. M. Industries, Paris, France

[21] Appl. No.: 126,993

[22] Filed: Mar. 3, 1980

[30] Foreign Application Priority Data

Mar. 23, 1979 [FR] France .............................. 79 07430

[51] Int. Cl.$^3$ .......................................... C07C 103/52
[52] U.S. Cl. ........................ 260/112.5 S; 260/112.5 R
[58] Field of Search ................... 260/112.5 R, 112.5 S

[56] References Cited

U.S. PATENT DOCUMENTS

3,917,578 11/1975 Immer et al. ................. 260/112.5 S
3,917,581 11/1975 Immer et al. ................. 260/112.5 S
4,216,141 8/1980 Rivier et al. ................. 260/112.5 R Primary Examiner—Delbert R. Phillips
Attorney, Agent, or Firm—Lewis H. Eslinger

[57] ABSTRACT

The present invention relates to a new process for the stepwise preparation of somatostatin enabling a product of high purity to be obtained, with high yields, from cysteine in 14 position whose acid function is protected by the phenylazobenzylsulfonylethyloxy group and thiol function is protected by the acetamidomethyl group, all the peptide coupling reactions being effected in liquid phase in the dimethylformamide, the intermediate peptides being precipitated by addition of a second solvent and purified in solid phase by washing with the aid of suitable solvents dissolving the impurities.

15 Claims, 2 Drawing Figures

PROCESS FOR THE PREPARATION OF SOMATOSTATIN

The present invention relates to a new process for the preparation of somatostatin.

Somatostatin has been isolated by Guillemin's team from fragments of ovine hypothalamus [reports of the Academie des Sciences de Paris, 275, 2913 (1972)]. The same team indicated the structure thereof which corresponds to a cyclic tetradecapeptide with a disulfide bond connecting the cysteine groups in 3 and 14 positions:

Ala—Gly—Cys—Lys—Asn—Phe—Phe—Trp—Lys—Thr—Phe—Thr—Ser—Cys—OH
 1    2    3    4    5    6    7    8    9    10   11   12   13   14

In this formula, all the aminoacids, with the exception of glycine, are in the L configuration and the abbreviations used for the aminoacids are those recommended by the IUPAC-IUB Commission of biochemical nomenclature [Journal of Biological Chemistry, 247, 977, (1972)].

Somatostatin possesses a wide variety of biological effects particularly at the level of the inhibition of the secretion of the growth hormone and the inhibition of the secretions of insulin and glucagon, as well as the inhibition of certain digestive secretions.

Consequently, somatostatin has proved particularly interesting as therapeutic agent, particularly for the treatment of acromegaly, diabetes, and in gastroenterology. It has therefore proved necessary to produce sufficient quantities of very pure somatostatin in order to pursue the clinical investigations of the product.

Different synthesis of somatostatin have already been described.

Certain proposed methods use solid phase synthesis (U.S. Pat. Nos. 3,862,925 and 3,904,594 in particular), whilst others take place in liquid phase according to the fragment technique [Helvetica chemica Acta 57, 730 (1974), or Biochemical Biophysical Research Communication 54, 234 (1973) etc . . . . ] Finally, a stepwise process has recently been mentioned [International Journal of Peptides and Proteins Research, 11, 329 (1978)].

However, none of these different processes are adapted to a large-scale industrial production of somatostatin.

It is known that the processes of synthesis of peptides in solid phase are not transposable to the industrial scale, particularly due to the difficulties encountered in splitting the polypeptide from its support after the elongation phase. The splitting necessitates energetic means and is accompanied by a considerable degradation leading to low yields and requiring subsequent purifications which are long and difficult.

Similarly, the different liquid phase synthesis known heretofore lead to somatostatin only with very low yields and require numerous and laborious purifications during the intermediate phases.

It is an object of the process according to the present invention to overcome all these difficulties and to enable considerable quantities of high purity somatostatin to be obtained. This process is a so-called stepwise process from the C terminal, wherein, from the beginning of the synthesis, a protector group of the acid function of cysteine in 14 position is used, which renders the molecule insoluble in water and the usual organic solvents with the exception of dimethylformamide and dimethylsulfoxide. The peptide coupling reactions are effected in solution in dimethylformamide and the product of the reaction is isolated either by evaporation of the dimethylformamide, or by precipitation by addition of a second solvent which renders it insoluble. The crude peptide thus obtained is purified by solid phase washings with the aid of suitable solvents which dissolve the impurities.

This technique therefore presents, at washing level, the same advantages as the solid phase synthesis without presenting the drawbacks thereof (risk of incomplete reaction at coupling level, in particular).

The yields obtained at each step are excellent and are between 90 and 98% of the theoretical ones.

In the process used, the hydroxyl functions of the serine and of the two molecules of threonine do not need to be protected, this representing an important advantage as these protections are always difficult to effect. The protections of the side chains of the two molecules of lysine ($\omega$-amine function) and of the terminal acid function of cysteine in 14 position have been chosen so as to resist the necessary acid treatments during the elongation phases to release the temporary protections of the $\alpha$-amino functions.

They are therefore protector groups cleavable only in a strong basic medium, namely the methanesulfonylethyloxycarbonyl (MSC) group for the $\omega$-amines of the molecules of lysine and phenylazobenzylsulfonylethyloxy (OPSE) group for the acid function of cysteine in 14 position. It is the latter group which from the beginning, gives in particular their character of insolubility to the different intermediate peptides obtained in the course of the elongation phase.

Finally, the two thiol groups of the molecules of cysteine in 3 and 14 positions have been protected by a group which resists both the acid and basic conditions, in order to be able to be conserved until the end of the synthesis. The protector group thus chosen is the acetamidomethyl (Acm) group.

The first element of the synthesis is constituted by p-phenylazobenzylsulfonylethyl N-t-butoxycarbonyl S-acetamidomethyl L-cysteinate.

This compound is novel and is obtained by condensation of N-t-butoxycarbonyl S-acetamidomethylcysteine on p-phenylazobenzyl-sulfonylethanol in the presence of a dehydration agent such as dicyclohexylcarbodiimide.

This compound is obtained with an excellent yield; it is sparingly soluble in water and is orange-yellow in colour, facilitating the chromatographic follow-ups. Finally, the protector group of the tertiobutyloxycarbonyl amine may easily be eliminated with the aid of a strong acid, such as trifluoroacetic acid or formic acid containing 1% of hydrochloric acid.

From this starting product, the polypeptide chain is elongated by coupling the following amino acid, suitably protected, if necessary.

Each coupling phase is followed by a selective operation of release of the amine which will come into reaction upon the creation of the following peptide bond. Operation is carried out in a strong acid medium such as trifluoroacetic acid or formic acid with 1% of hydrochloric acid.

The temporary protector groups of the α amino functions, cleavable in acid medium, are chosen from the family of carbamates. These are either the N-tertiobutoxycarbonyl (Boc) group, or the N-α-biphenylisopropyloxycarbonyl (B Poc) group.

As soon as the L-tryptophane is in place (8 position), it becomes essential, at the amount of the cleavage phases of the intermediate protector groups, to use chemical additives which protect the indole nucleus from parasitic reactions specific of this heterocycle.

Thus, the addition of anisole in the medium prevents the reactions giving rise to free radicals, whilst the use of thiols such as ethanedithiol or mercapto-ethanol avoids the parasitic oxidations of this heterocycle.

It is generally preferred to use, in the coupling phases, the suitable protected α-aminoacids in the form of activated esters.

The reaction solvent is chosen so as to maintain in solution both the reagents and the reaction products. The choice solvents, taking into account the character of insolubility of the polypeptides obtained, are dimethylformamide and dimethylsulfoxide.

The use of a coupling activator such as hydroxybenzotriazol, has a beneficial effect on the speed of reaction, whilst minimising the risks of racemization.

Finally, it is advantageous to introduce the last two aminoacids together in the form of activated dipeptide.

All the operations are shown in the following synthesis schemes I and II.

SCHEME I

| Phe | Phe | Trp | Lys | Thr | Phe | Thr | Ser | Cys | | Yield | Accumulated yield | Example n° |
|-----|-----|-----|-----|-----|-----|-----|-----|-----|-----|-------|------|----|
| | | | | | | | Boc—OH⁻  H—  DCCI | Acm / OPse | | 97 | 97 | 2 |
| | | | | | | | Boc— | Acm / OPse | | 80 | 77.6 | 3 |
| | | | | | | Boc—ONsu  H— | | Acm / OPse | | 97 | 75.27 | 4 |
| | | | | | | Boc— | | Acm / OPse | | 98 | 73.76 | 5 |
| | | | | | Boc—ONp  H | | | Acm / OPse | | 94 | 69.33 | 6 |
| | | | | | Boc | | | Acm / OPse | | 90 | 62.39 | 7 |
| | | | | Boc—ONsu  H— | | | | Acm / OPse | | 97 | 60.51 | 8 |
| | | | | Boc | | | | Acm / OPse | | 90 | 54.46 | 9 |
| | | | Boc-ONp(Msc)H | | | | | Acm / OPse | | 97 | 52.82 | 10 |
| | | | Boc— Msc | | | | | Acm / OPse | | 88 | 46.48 | 11 |
| | | Boc—ONp  H Msc | | | | | | Acm / OPse | | 98 | 45.55 | 12 |
| | | Boc— Msc | | | | | | Acm / OPse | | 85 | 38.71 | 13 |
| Bpoc—ONp  H | | Msc | | | | | | Acm / OPse | | 92 | 31.61 | 15 |
| Bpoc— | | Msc | | | | | | Acm / OPse | | 93 | 33.12 | 16 |

SCHEME II

| Ala | Gly | Cys | Lys | Asn | Phe | Phe | Trp | Lys | Thr | Phe | Thr | Ser | Cys | Yield | Accumulated yield | Example n° |
|---|---|---|---|---|---|---|---|---|---|---|---|---|---|---|---|---|
| | | | | | Boc | ONp-H | | Msc | | | | | Acm / OPse | 97 | 32.13 | 17 |
| | | | | | Boc | | | Msc | | | | | Acm / OPse | 95 | 30.52 | 18 |
| | | | | Boc | ONp-H | | | Msc | | | | | Acm / OPse | 100 | 30.52 | 20 |
| | | | | Boc | | | | Msc | | | | | Acm / OPse | 87 | 26.55 | 21 |
| | | | Boc | Msc / ONp-H | | | | Msc | | | | | Acm / OPse | 100 | 26.55 | 22 |
| | | | Boc | | | | | Msc | | | | | Acm / OPse | 92 | 24.43 | 23 |
| | | Boc | Acm / ONp-H | | | | | Msc | | | | | Acm / OPse | 100 | 24.43 | 24 |
| | | Boc | Acm | | | | | Msc | | | | | Acm / OPse | 93 | 22.72 | 25 |
| | Boc | OTcp H | Acm | | | | | Msc | | | | | Acm / OPse | 100 | 22.72 | 26 |
| Boc | | | Acm | | | | | Msc | | | | | Acm / OPse | 93 | 21.58 | 27 |
| Boc | | | Acm | | | | | Msc | | | | | Acm / OPse | 100 | 21.58 | 28 |

The yields are excellent at all levels and the purity of the products is satisfactory. The controls are made by thin layer chromatography on silicagel plates in different elution media.

A variant of the process consists in separately effecting the synthesis of the heptapeptides 1 to 7 and 8 to 14 likewise according to the stepwise principle. The two heptapeptides are then coupled by a suitable chemical agent to form tetradecapeptide.

This variant presents the advantage of not subjecting the tryptophane, an aminoacid particularly sensitive to oxidation and to reactions giving rise to free radicals, to a series of reactions for carrying out the phases of deprotection subsequent to each coupling of the aminoacids 1 to 7.

Heptapeptide 8 to 14:

is identical to the intermediate heptapeptide of the complete stepwise strategy.

Heptapeptide 1 to 7:

is obtained by a particular process in which the terminal acid is not protected during the elongation phase, this making it possible to carry out the coupling reactions in liquid phase and the washings in solid phase.

One starts from the known dipeptide H—Phe—Phe—OCH₃, on which is reacted the orthonitrophenolic ester of orthonitrophenylsulfenamino asparagine in dimethylformamide. The tripeptide is isolated by precipitation with ether and purified by washings in solid phase. This tripeptide is entirely deprotected by a basic treatment (saponification of the ester), then by acidolysis which releases the amine function of the lysine.

This tripeptide H—Asn—Phe—Phe—OH is used in its terminal free acid form for the following operations.

Each amino acid is introduced in the form of activated ester and the reaction is conducted in the presence of an accelerator such as hydroxybenzotriazol and in the presence of a non-racemizing organic base such as N-ethylmorpholine.

All the different stages are brought together on the following synthesis scheme III.

SCHEME III

| Ala | Gly | Cys | Lys | Asn | Phe | Phe |  | Yield | Accumulated Yield | Example n° |
|---|---|---|---|---|---|---|---|---|---|---|
|  |  |  |  | NPs | ONp |  | O—CH₃ |  |  |  |
|  |  |  |  | NPs |  |  | O—CH₃ | 82.1 | 82.1 | 32 |
|  |  |  |  |  |  | ↓OHNa |  |  |  |  |
|  |  |  |  | NPs |  |  | OH | 94 | 77.17 | 33 |
|  |  |  |  |  | ↓HCl |  |  |  |  |  |
|  |  |  | Msc |  |  |  |  |  |  |  |
|  |  |  | Boc—ONp | H |  |  | OH | 98.8 | 76.24 | 34 |
|  |  |  | Msc |  |  |  |  |  |  |  |
|  |  |  | Boc |  |  |  | OH | 95 | 72.42 | 35 |
|  |  | Acm | Msc |  |  |  |  |  |  |  |
|  |  | Boc—ONp |  |  | ↓TFA |  | OH | 92 | 66.63 | 36 |
|  |  | Acm | Msc |  |  |  |  |  |  |  |
|  |  | Boc |  |  |  |  | OH | 96.3 | 64.16 | 37 |
|  |  |  |  |  | ↓TFA |  |  |  |  |  |
| Boc | OTrp |  |  |  |  |  | OH | 98 | 62.87 | 38 |
|  | Acm | Msc |  |  |  |  |  |  |  |  |
| Boc |  |  |  |  |  |  | OH | 98 | 61.62 | 39 |

The coupling between the two heptapeptides may be effected in dimethylformamide in the presence of a coupling agent such as dicyclohexylcarbodiimide, or with the aid of an activator of the carboxylic function such as hexafluorophosphate of benzotriazolyloxy (tridimethylamino)-phosponium.

The tetradecapeptide obtained by this process is absolutely identical to that obtained by the complete stepwise process.

Whatever the variant used, the following protected tetradecapeptide is thus attained:

A treatment in a strong acid medium such as trifluoroacetic acid makes it possible to release the amine function of the alanine in 1-position. By action of a strong base such as baryte, for a relatively short time (15 to 30 mins.) and at ambient temperature on a solution of the product in the dimethylformamide, both the protector groups of the side chains of the two lysines and the ester on the cysteine in 14 position are eliminated.

In the following scheme IV, all the operations from the protected tetradecapeptide are summarised. The crude somatostatin thus obtained necessitates only a permeation chromatography on gel on Sephadex G 25 to obtain a high purity product whose titre is greater than 98% by HPLC determination.

SCHEME IV

|  | Yield | Accumulated Yield | Example n° |
|---|---|---|---|
| H—Ala—Gly—Ser(Acm)—Lys(Msc,Acm)—Asn—Phe—Phe—Trp(OH)₂—Lys(Msc,Ba)—Thr—Phe—Thr—Ser—Cys(Acm)—OPse | | | |
| H————————OH | 48% | 10.36 | 29 |
| (S—Ag), (NO)₃ S—Ag, S—Ag | | | |
| H————————OH | / | / | / |
| SH, SH₂, SH, SH | | | |
| H————————OH | 86% | | 30 |
| oxidation S—S | | | |
| H—Ala—Gly—Cys—Lys—Asn—Phe—Phe—Trp—Lys—Thr—Phe—Thr—Ser—Cys—OH | 46% | 4.77 | 31 | with respect to n°29

Di-S-acetamidomethyl-3,14-dihydrosomatostatin is thus obtained which is subjected to a purification before the final steps are carried out.

Different methods may be used, for purification, such as countercurrent distribution, partition chromatography on gel, chromatography on ion exchangers, etc. On considerable quantities, the countercurrent distribution has proved to be the choice method and enables a product to be obtained of purity greater than or equal to 98%. The release of the thiol function of the two cysteines is easily obtained according to known methods, namely by treatment by a salt of heavy metal such as mercury or silver. It may be possible to isolate the salt of dihydrosomatostatin with the metal. The latter may be conserved, if necessary, and without alteration, for several weeks at +4°, away from light.

A treatment by hydrogen sulfide makes it possible to eliminate the metal in the form of insoluble sulfide easy to eliminate.

The solution thus obtained contains dihydrosomatostatin which may be isolated by evaporation at ambient temperature.

The solution is most often subjected to final bridging in disulfide using known techniques of oxidation already used for the somatostatin itself or for other polypeptides such as vasopressin or oxytocin. For example, the oxygen of the air may be used, or potassium ferricyanide. In any case, operation should be carried out in a very dilute solution so as to minimise the polymerisation reactions to a maximum.

The process thus described makes it possible to prepare large quantities of somatostatin by making thorough purifications at only two levels:
  di-S-acetamidomethyl-3,14 dihydrosomatostatin,
  somatostatin itself.

In all the other steps, the phases of purification are limited to washing operations in heterogeneous phase.

The features and advantages of the process according to the invention will be more readily understood on reading the following examples, in which the following abbreviations will be used.

Protector groups:

Acm=acetamidomethyl
Boc=t-butoxycarbonyl
OPse=phenylazobenzylsulfonylethoxy
ONsu=N-succinimidoxy
ONp=nitro-4 phenoxy
OTcp=trichloro-2,4,5-phenoxy
Nps=o-nitrophenylsulfenyl
Msc=2-(methylsulfonyl) ethoxycarbonyl Eluents used in chromatography on a thin layer of silica Composition by volume
Truth: chloroform: 95—methanol: 5—acetic acid: 3.
BEW: 2-butanol: 72—acetic acid: 7—water: 21
BPEW 1: 1-butanol: 50—acetic acid: 12—pyridine: 12—water: 25
EBPEW: ethyl acetate: 42—1-butanol: 24—pyridine: 21—acetic acid: 6—water: 10

EPAW 2: Ethyl acetate: 70—pyridine: 16—formic acid: 8—water: 6
EPAW 1: ethyl acetate: 63—pyridine: 21—formic acid: 10—water: 6

Various abbreviations

Fc: melting point in capillary tube
DMF: dimethylformamide
DCCI: dicyclohexylcarbodiimide
AcOH: acetic acid
TFA: trifluoroacetic acid

EXAMPLE 1 p-phenylazobenzylsulfonylethyl (L)-N-t-butoxycarbonyl S-acetamidomethylcysteinate (a) N-hydroxymethylacetamide 250 g of acetamide, 150 g of polyoxymethylene and 2.5 g of potassium carbonate are pulverised together and melted at 100° C. After 1 hour at this temperature and cooling towards 50°-50° C., 0.5 ml of 12 N aqueous potash is added and the mixture is left overnight in the refrigerator. The set solid is taken up in the minimum of pure acetone (about 200 ml) to dissolve it at ambient temperature. The product crystallizes by cooling for a few hours at −30° C., it is then filtered rapidly and dried, 170 g are thus obtained: Fc 45°–50° C.

A second jet of about 50 g may be obtained by concentrating the solvent.

(b) (L)-S-acetamidomethylcysteine hydrochloride

H—Cys (Acm)—OH, Cl H 75 g (0.84 mole) of acetamido methanol in solution in 300 ml of dioxane are added drop by drop at ambient temperature to a well stirred mixture of 88 g (0.5 mole) of hydrochloride of L-cysteine monohydrate in 1 250 ml of dioxane, 22 ml of concentrated hydrochloric acid and 40 ml of water. Stirring is continued for 30 mins., the oil formed is decanted and the solvent that it contains is evaporated in a rotary evaporator at 30° C. The residue is taken up in ethanol which is evaporated in turn to dehydrate the product: it crystallizes progressively and is filtered in vacuo, washed with isopropanol, then with ether and dried in vacuo.

90 g are thus obtained (yield: 80%); Fc 162°–165° C.
$[\alpha]_D^{25} = -27.5°$ (C=1, water).

A sample recrystallized in the 80/20 (volume/volume) isopropanol-water mixture furnishes a product of Fc 166°–169° C.
$[\alpha]_D^{25} = -27°$ (C=1, water)

(c) (L)-N-t-butoxycarbonyl S-acetamidomethylcysteine 18.2 g (0.08 mole) of hydrochloride of acetamidomethylcysteine in solution in 130 ml of a 50/50 (volume/volume) dioxane-water mixture are taken to 30°–35° C. in a water bath and the pH adjusted to 10.0 by 4 N NaOH. 12.3 g (11.2 ml, 0.088 mole) of t-butyl azidoformate are then added and the pH maintained at 10.0 by additon of 4 N NaOH. The reaction is complete in a period of between 18 and 30 hrs. (function of the temperature ). 70 ml of water are then added and the mixture is washed twice with 100 ml of ether to eliminate the excess of reagent. The aqueous phase cooled to 0°+5° C. is acidified in the presence of ethyl acetate to pH 2.5 by a 4 N solution of potassium bisulfate, then the aqueous phase is extracted three times by ethyl acetate. The organic extracts collected are washed with a saturated solution of sodium chloride (twice), dried and evaporated in partial vacuum leaving an oil which crystallizes gradually in the presence of anhydrous ether.

19.5 g (83%); Fc 112°–114° C.
$[\alpha]_D^{25} = -29.5°$ (C=1, CH$_3$OH).
$[\alpha]_D^{25} = -33.6°$ (C=1, H$_2$O).

(d) p-phenylazobenzylsulfonylethyl (L)N-t-butoxycarbonyl S-acetamido-methylcysteinate 32 g (0.110 mole) of Boc—Cys—OH are dissolved in 350 ml of pure pyridine followed by 30.4 g (0.100 mole) of PseOH. When all is homogeneous, the solution is cooled to 0° C. and treated progressively by 21.6 g (0.105 mole) of dicyclohexylcarbodiimide in solution in 40 ml of pure pyridine. The solution is stirred overnight in the refrigerator.

A CCM/AcOeT—CH$_3$OH: 96/4 (volume/volume) control makes it possible to verify the total conversion of Pse OH (Rf$v$0.50–0.55) into the expected product (Rf$v$0.42–0.50). If it is not complete, add a little in excess as the elimination of the residual PseOH is difficult.

The isolation of the product is effected in the following manner: the dicyclohexylurea (DCU) is filtered, the pyridine evaporated in vacuo at 30° C., the residue taken up in ethyl acetate and the DCU filtered again, then the solution washed successively by a solution of bisulfate-sulfate of potassium (ph=2.0), water, a solution of 5% sodium bicarbonate in water, then water and dried over magnesium sulfate. After filtration, the solvent is evaporated, the red gum obtained solidifies progressively by contact with 400 ml of anhydrous ether. The gel obtained is pulverised and filtered, rinsed with anhydrous ether and dried.

Weight: 53.3 g; yield 92%; Fc 75°–77° C.
$[\alpha]_D^{25} = -16°$ (C=1, AcOH).
$[\alpha]_D^{25} = -24°$ (C=1, CH$_3$OH).
CCM/AcO Et-MeOH Rf=0.50; BEW$_1$ Rf=0.69
Truth Rf=0.50; BPEW$_1$Rf=0.77

EXAMPLE 2

(L)-S-acetamidomethylcysteinate of p-phenylazobenzylsulfonylethyl, hydrochloride -continued 5.78 g of Boc—Cys—OPse are added rapidly (1 to 2 mins.) to a solution of 1 ml of concentrated hydrochloric acid in 100 ml of formic acid (98% pure) at ambient temperature.

After 10 mins. at this temperature, the reaction is completed. The solvent is evaporated in vacuo as quickly as possible at a temperature $\leq 30°$ C. The oily residue taken up in 15 ml of methanol is poured drop by drop in 150 ml of anhydrous ether stirred at 0° C. The product is filtered, rinsed with anhydrous ether and dried in the presence of phosphoric anhydride in vacuo. 5.0 g (97%) of a hydrochloride are thus obtained, of Fc 160°–162° C. (decomposition).

CCM/BEW$_1$ Rf = 0.36 | single product
BPEW$_1$ Rf = 0.62

EXAMPLE 3

N-t-butoxycarbonyl L-seryl S-acetamidomethyl L-cysteine p-phenylazobenzyl-sulfonylethylester Boc—Ser—Cys—OPse 5.15 g (0.01 mole) of hydrochloride of S-acetamidomethylcysteine are treated in solution in 60 ml of anhydrous pure DMF by a solution of 1.15 g of N-ethylmorpholine, then cooled to $-10°$ C. and then treated with 2.05 g of N-butoxycarbonyl L-serine (added rapidly) then drop by drop in 5–10 mins. with a solution of 2.47 g of DCCI and 2.70 g of hydroxybenzotriazol in 20 ml of pure DMF.

After 1 hr. at $-10°$ C., the temperature is allowed to rise progressively to ambient temperature (20° C.) avoiding any heating.

The reaction is complete in 6 hrs. The DMF is then evaporated under high vacuum at 30°–35° C. and the residue taken up in 200 ml of ethyl acetate. The dicyclohexylurea is filtered and the following washings are carried out: aqueous sulfate and bisulfate of potassium, water, 5% aqueous bicarbonate of sodium, water, each washing being repeated two or three times.

After drying over magnesium sulfate at ambient temperature, the solvent is concentrated to about 50 ml. The product precipitates in a gel by cooling over-night at 0° C. It is filtered, rinsed with a little ethyl acetate, then anhydrous ether and dried in vacuo without heating.

Yield: 5.3 g (80%); Fc 111°–113° C.

CCM/BEW$_1$Rf = 0.63
BPEW$_1$RF = 0.70 | Reindel-Hoppe detector
EPAW$_2$Rf = 0.74

In these various systems, the product contains a little dicyclohexylurea (Rf 0.08 to 0.86) which will be eliminated at the following stage.

$[\alpha]_D^{25} = -25.5$ (C=1, CH$_3$OH).

EXAMPLE 4

L-seryl S-acetamidomethyl L-cysteinate of p-phenylazobenzylsulfonylethyl, trifluoroacetate H—Ser—Cys—OPse, CF$_3$COOH

38.5 g of Boc—Ser—Cys—OPse are rapidly added to 300 ml of trifluoroacetic acid previously cooled towards 0° C. (the temperature rises towards 18° C. on such quantities). After 3 to 5 mins., the acid is evaporated at 20° C. at 15 mm. The residue is taken up in anhydrous ether, the product solidifying on contact therewith. It is filtered and rinsed with anhydrous ether several times and dried.

Yield: 38.5 g (97%).
CCM/EPAW$_2$ Rf=0.30
BPEW$_1$ Rf=0.60
EBPEW Rf=0.50

EXAMPLE 5

N-t-butoxycarbonyl L-theonyl L-seryl S-acetamidomethyl L-cysteine, p-phenylazobenzylsulfonylester Boc—Thr—Ser—Cys—OPse 6.80 g of trifluoroacetate of H—Ser—Cys—OPse are dissolved in 100 ml of pure DMF. Whilst cooling in an ice bath, 2.52 ml of N-ethylmorpholine and 3.79 g of Boc—Thr—ONSu are successively added. The reactional medium is conserved at ambient temperature for 2 hrs. Isolation is effected by evaporation of the DMF at 30° C. and taking up in ice. Filtering is effected in vacuo then washing with water with a solution of bisulfatesulfate-sulfate of potassium (pH=2), with water, 5% aqueous sodium bicarbonate and finally with water twice. After drying in the air, then on phosphoric anhydride in vacuo, 7.5 g are obtained (98%); Fc=136°–138° C.
CCM/EPAW$_2$ Rf=0.70
BEW$_1$ Rf=0.69
EBPEW Rf=0.86

EXAMPLE 6

L-threonyl L-seryl S-acetamidomethyl L-cysteinate of p-phenylazobenzylsulfonylethyl, trifluoroacetate CF$_3$COOH, H—Thr—Ser—Cys—OPse 7.67 g (0.01 mole) of Boc—Thr—Ser—Cys—OPse are added to 60 ml of trifluoroacetic acid cooled in an ice bath, with stirring. The cold bath is removed and the solution conserved for 5 mins. before evaporating the trifluoroacetic acid. The residue thus obtained is taken up in ether in the presence of which it is triturated, filtered and washed abundantly, then dried.

7.34 g of trifluoroacetate are obtained (94%).
CCM/EPAW$_2$ Rf=0.30, pure product
EPAW$_1$ Rf=0.52, pure product

EXAMPLE 7

N-t-butoxycarbonyl L-phenylalanyl L-threonyl L-seryl S-acetamidomethyl L-cysteine, p-phenylazaobenzylsulfonylethylester 7.81 g (0.01 mole) of trifluoroacetate of H—Thr—Ser—Cys(Acm)—OPse are dissolved in 90 ml of anhydrous DMF and treated at 0° C. with 2.52 ml of N-ethylmorpholine, then with 4.64 g of Boc—Phe—ONp.

After a night in the refrigerator, the product is isolated by evaporation of the DMF under high vacuum at 30° C. maximum washings of the solid obtained with water, a solution of bisulfate-sulfate of potassium, water, aqueous sodium bicarbonate, water and, after a light drying, with isopropanol and, finally, with ether.

Thus, 8.22 g are obtained (90%); Fc 153°–155° C.
CCM/EPAW$_1$ Rf=0.84
EPAW$_2$ Rf=0.67
BEW$_1$ Rf=0.75
BPEW$_1$ Rf=0.75
$[\alpha]_D^{25} = 16.0°$ (C=1, CH$_3$COOH).

EXAMPLE 8

L-phenylalanyl L-threonyl L-seryl S-acetamidomethyl L-cysteinate of p-phenylazobenzylsulfonylethyl, trifluoroacetate are added to 55 ml of glacial trifluoroacetic acid with stirring. The mixture is then conversed for 6 to 10 mins. leaving it to heat up, then it is evaporated in vacuo at 20°–25° C. The residue is taken up in a large quantity of ether, triturated, filtered and washed with ether.

9.0 g (97%) of a pure product are thus obtained.
CCM/EPAW$_1$ Rf=0.47
EPAW$_2$ Rf=0.39
BPEW$_1$ Rf=0.65
EBPEW Rf=0.65
$[\alpha]_D^{25} = -18.5°$ (C=1, CH$_3$OH).

EXAMPLE 9

N-t-butoxycarbonyl L-threonyl L-phenylalanyl L-threonyl L-seryl S-acetamidomethyl L-cysteine p-phenylazobenzylsulfonylethylester 9.28 g of trifluoroacetate of in solution in 100 ml of anhydrous DMF are treated successively in an ice bath with 2.52 ml of N-ethylmorpholine, then with 3.80 g of Boc—Thr—ONSu. The solution is conserved overnight in the refrigerator. The solvent is evaporated under high vacuum at 30° C., the residue taken up in ice until solidification, filtered, washed with water, with an aqueous solution of bisulfate—sulfate of potassium, with water, with aqueous sodium bicarbonate, with water, then 2×5 ml of isopropanol and finally with ether, and dried.

9.1 g (90%) of product are thus obtained. Its purity is generally not satisfactory in CCM and it must undergo washings with the following mixtures: isopropanol-water: 50/50, then 75/25, then 100/0 (50 to 100 ml per wash).

Yield: 86%

The pure product presents the following characteristics:

CCM/EPAW$_1$ Rf=0.79
EPAW$_2$ Rf=0.63
BEW$_1$ Rf=0.66
TRUTH Rf=0.05
Fc 169°–172° C.
$[\alpha]_D^{25} = -20°$ C. (C=1, AcOH).

EXAMPLE 10

L-threonyl L-phenylalanyl L-threonyl L-seryl S-acetamidomethyl L-cysteinate of p-phenylazobenzylsulfonylethyl, trifluoroacetate are dissolved in 160 ml of a 50/50 (volume/volume) mixture of T.F.A., methylene chloride previously cooled towards 5° to 10° C. After 30 mins. at ambient temperature, the reaction is complete. The solvents are evaporated in vacuo and the residue taken up in isopropanol which is evaporated. Taking up is then effected in anhydrous ether, followed by filtering, washing in a large quantity of ether and drying.

20.3 g (98%) are obtained.
CCM/EPAW$_1$ Rf=0.50
EPAW$_2$ Rf=0.33
EBPEW Rf=0.69
$[\alpha]_D^{25} = -9.8°$ (C=1, AcOH).

EXAMPLE 11

N-α-t-butoxycarbonyl N-ω-methylsulfonylethoxycarbonyl L-lysyl L-threonyl L-phenylalanyl L-threonyl L-seryl S-acetamidomethyl L-cysteinate of p-phenylazobenzyl sulfonylethyl 10.29 g of the trifluoroacetate of the pentapeptide in solution in 100 ml of anhydrous DMF are treated successively at 0° C. with 2.52 ml of N-ethylmorpholine, then 6.2 g of

The reaction is conserved at ambient temperature for 15 to 20 hrs. Isolation is then effected in the usual manner: evaporation of the solvent under a high vauum at 30° C., stirring in the presence of ice, filtration, abundant washings with water, with the aqueous solution of sulfate-bisulfate of potassium (pH2), then again with water, followed by two washings with 100 ml of isopropanol and, finally abundantly with ether.

11.4 g (88%) of a product are thus obtained which must generally undergo repeated washings with acetone (from 26 to 50 ml).

A pure product is thus obtained, with a yield of 80 to 85%; Fc 172°–174° C.
CCM/EPAW$_1$ Rf=0.75
EPAW$_2$ Rf=0.50
BEW$_1$ Rf=0.57
$[\alpha]_D^{25}$=−19.5° (C=1, AcOH).

EXAMPLE 12

N-ω-methylsufonylethoxycarbonyl L-lysyl L-threonyl L-phenylalanine L-threonyl L-seryl S-acetamidomethyl L-cysteinate of p-phenylazobenzylsulfonylether, trifluoroacetate 6.47 g (5 millimoles) of are added to 52 ml of trifluoroacetic acid, with stirring. After total dissolution (2 to 3 mins.), the acid is evaporated in vacuo at 20° C. and the residue taken up in isopropanol filtered in vacuo, rinsed twice with the same solvent then with ether and dried in the presence of potash in vacuo.

The product weighs 6.40 g (97%) and is virtually pure in
CCM/EPAW$_2$ Rf=0.25
EPAW$_1$ Rf=0.50

EXAMPLE 13

N-α-t-butoxycarbonyl L-triptophanyl N-ω-methylsulfonyl-ethoxycarbonyl L-lysyl L-threonyl L-phenylanyl L-threonyl L-seryl S-acetamidomethyl L-cysteinate of p-phenylazobenzylsulfonylethyl

13.075 g of trifluoroacetate of are placed in solution in 130 ml of anhydrous DMF and treated in an ice bath with 2.5 ml of N-ethylmorpholine, 5.11 g of Boc—Trp—ONp and 2.70 g of hydroxybenzotriazol. After about 1 hr. at ambient temperature, the reaction is complete, the solvent evaporated, the residue taken up in ice solidifies gradually; it is finely ground, filtered, washed abundantly in water then, after a light drying, twice with 120 ml of lukewarm isopropanol, then with fractions of 100 ml of lukewarm acetone until satisfactory purity in CCM (from 4 to 10 washings according to the experiments). Thus, 12.6 g (85%) of the product of the titre presenting the following characteristics are obtained:
CCM/EAPW$_2$ Rfv0.50
$[\alpha]_D^{25}$=−17.5° (C=1, AcOH).

EXAMPLE 14

N-α-biphenylisopropyloxycarbonyl L-tryptophanyl N-ω-methylsulfonylethoxy-carbonyl L-lysyl L-threonyl L-phenylalanyl L-threonyl L-seryl S-acetamidomethyl L-cysteinate of p-phenylazobenzylsulfonylethyl.

1.307 g of trifluoroacetate of in solution in 13 ml of anhydrous DMF are treated at 0° C. with 0.25 ml of N-ethylmorpholine and 0.666 g of Bpoc—Trp—ONp. After a dwell period of 48 hrs. at +4° C. or 24 hrs. at ambient temperature, the reaction is generally completed. After evaporation of the solvent under high vacuum at 30° C., the residue solidified by stirring in the presence of ice. The precipitate is filtered, washed in a large quantity of water then with aqueous solutions of 5% sodium bicarbonate and of citrate buffer pH 3.5, and, finally, with water. After drying, it is washed three times with 10 ml of lukewarm isopropanol, then three times with 10 ml of lukewarm acetone, which is generally sufficient to obtain a correct purity.

After drying, 1.37 g (85%) are thus obtained. This product is characterized by:
Fc 158°–160° C.
$[\alpha]_D^{25}$=−16.5° (C=1, AcOH).
CCM/BEW$_1$ Rf=0.70
EPAW$_1$ Rf=0.76
EBPEW Rf=0.77

EXAMPLE 15

L-tryptophanyl N-ω-methylsulfonylethoxycarbonyl L-lysyl L-threonyl L-phenylalanyl L-threonyl L-seryl S-acetamidomethyl L-cysteinate of p-phenylazobenzylsulfonylethyl, trifluoroacetate.

1.30 g of the heptapeptide of Example 14 is added in about one minute to a mixture previously cooled to 5° C. of 13 ml of trifluoroacetic acid, 1.3 ml of ethanedithiol and 0.65 ml of anisole. After 2 mins. of stirring at this temperature, the volatile reagents are evaporated in vacuo without heating and the residue taken up in twice 15 ml of methanol which is evaporated each time in vacuo. The residue, triturated in the presence of 15 ml of isopropanol, is filtered. It is then washed three times with 15 ml of the same lukewarm solvent (40° C. about) then with ether and dried.

1.10 g (92% of the trifluoroacetate are thus obtained, which product proves to be pure in CCM in the following mixtures:
EPAW$_1$ Rf=0.36
BEW$_2$ Rf=0.36

EXAMPLE 16

α-Biphenylisopropyloxycarbonyl L-phenylalanyl L-triptophanyl ω-methyl-sulfonylethoxycarbonyl L-lysyl L-threonyl L-phenylalalanyl L-threonyl L-seryl S-acetamidomethyl L-cysteinate of p-phenylazobenzylsulfonylethyl.

13.4 g of the trifluoroacetate of the heptapeptide of Example 15 in solution in 130 ml of DMF are treated successively with 2.3 ml of N-ethylmorpholine, 2.43 of hydroxybenzotriazol and 4.25 g of Boc—Phe—ONp in an ice bath. After 1 hr. of dwell at ambient temperature, a CCM control shows that the reaction is completed. The DMF is then evaporated under high vacuum and the residue stirred in the presence of ice solidifies progressively. It is filtered, washed with water and dried, then washed twice with isopropanol and three times with lukewarm acetone (40° C.).

13.6 g (93%) of a product of correct purity in chromatography are thus obtained.
CCM/EPAW$_1$ Rf=0.77
EPAW$_2$ Rf=0.58
BPEW$_1$ Rf=0.69
BEW$_1$ Rf=0.67
EBPEW Rf=0.91
$[\alpha]_D^{25}$ = −9° (C=1, DMF).

EXAMPLE 17

13.4 g (8.2 moles) of the octapeptide of Example 16 are added to a mixture previously cooled to 5° C. of 130 ml of TFA, 13 ml of ethanedithiol, and 6.5 ml of anisole. Stirring is continued for 15 mins. at ambient temperature.

Evaporation is effected in vacuo at ambient temperature, then the residue is taken up twice in 70 ml of methanol, evaporating the solvent each time. The product is then taken up in isopropanol and the solid is filtered, washed twice with 70 ml of lukewarm isopropanol (40° C.). It is washed abundantly with anhydrous ether and dried.

13.1 g (97%) of pure product are thus obtained.
CCM/EPAW$_1$ Rf=0.38
EPAW$_2$ Rf=0.32
BEW$_1$ Rf=0.42
EBPEW Rf=0.75

EXAMPLE 18

13.1 g of trifluoroacetate of in solution in 130 ml of anhydrous DMF at 0° C. are treated successively with 2 ml of N-ethylmorpholine, 2.16 g of hydroxy benzotriazol and 3.70 g of Boc—Phe—ONp. Stirring is continued at ambient temperature for 1 hr. The DMF is then evaporated at 30° C. in vacuo and the oil residue crystallizes gradually in the presence of ice. The precipitate is filtered, washed abundantly with water and dried before being finely ground and washed twice with isopropanol, three times with methanol, then five times with acetone.

After drying, it weighs 13.5 g (95%).
CCM/EPAW$_2$ Rf=0.62
BPEW$_1$ Rf=0.70
EBPEW Rf=0.94
$[\alpha]_D^{25}$ = −9.2° (C=1, DMF).

EXAMPLE 19

A solution of 0.98 g of the trifluoroacetate of in 12 ml of DMF is treated at 0° C. with 0.15 ml of N-ethylmorpholine and 0.378 g of Bpoc—Phe—ONp. The reaction is completed after 24 hrs. at ambient temperature. After evaporation of the DMF at 30° C. in vacuo, the residue is crystallized in the presence of ice, filtered in vacuo, washed successively with glacial citrate buffer pH 3.5, with water, with a saturated solution of sodium bicarbonate, then with water and dried. The following washings, three times with 4 ml isopropanol, three times with 3 ml acetone and twice 5 ml of ether, furnish, after drying, a product which is again washed three times with 4 ml acetone.

Finally, 1.02 g (89%) of pure product are obtained;
CCM/EPAW$_1$ Rf=0.82
EPAW$_2$ Rf=0.58
$[\alpha]_D^{25}$ = −9.1° (C=1, DMF).
F. 222°–224° C. (decomposition)

EXAMPLE 20

TFA,

-continued

At the laboratory temperature, the following mixture is prepared: TFA: 300 ml, ethanedithiol 30 ml, anisole, 15 ml. 30 g of are added, the mixture is kept 20 mins. at laboratory temperature, then evaporated at 30° C. in vacuo to a residual volume of about 70 ml.

This residue is poured on 700 ml of 50/50 (volume/volume) mixture of 2-propanol/ethyl ether. The precipitate is drained, washed with the same mixture, then with ether alone.

After drying, 30.2 g (100%) are obtained.
CCM/EPAW$_2$ Rf=0.40.

EXAMPLE 21

30.2 g of TFA, are dissolved in 300 cm3 of DMF then treated successively with 4.3 cm3 of N-ethylmorpholine, 4.6 g of hydroxybenzotriazol, 7.2 g of Boc—Asn—ONp. After 30 mins. at laboratory temperature, the reaction is completed. The DMF is evaporated at 35° C. in vacuo up to a residual volume of about 100 ml. This solution is poured with stirring on a mixture of water-ice (500 ml), this causing the crystallization of the product. The solid is drained, washed abundantly with water then with 2-propanol (twice), methanol (twice) and acetone (three times).

After drying, 28 g (87%) are obtained.
CCM/EPAW$_2$ Rf=0.70
$[\alpha]_D^{22} = -16°$ (C) 1, DMF).

EXAMPLE 22

28.2 g of the decapeptide of Example 21 are treated with TFA (280 ml), ethanedithiol (28 ml) and anisole (14 ml) for 20 mins. at laboratory temperature. The evaporation of the TFA in vacuo at 30° C. is conducted to a residual volume of 50-60 ml. It is then poured on 500 ml of 50/50 (volume/volume) mixture of 2-propanol/ether. The precipitate is drained, washed and dried.

After drying, 28.5 g (100%) are obtained.
CCM/EPAW$_2$ Rf=0.60.

EXAMPLE 23

In 310 ml of anhydrous DMF are dissolved 30.5 g of the trifluoroacetate obtained in Example 22, then N-ethylmorpholine (4.05 ml) hydroxybenzotriazol (4.32 g) and (9.95 g) are added. The reaction is completed after 45 mins. at ambient temperature. The volume of the DMF is reduced to about 100 ml by evaporation in vacuo. The solution is poured on 600-700 ml of a mixture of water-ice. The solid is drained, washed in water then with methanol (three times) and acetone (three times).

After drying, 32 g (92%) are obtained.
CCM/EPAW$_2$ Rf=0.70
BEW$_1$ Rf=0.50
$[\alpha]_D^{25} = -14.5°$ (C=1, DMF).

EXAMPLE 24

In a mixture of dichloromethane (150 ml), ethanedithiol (18 ml) and anisole (9 ml), 30.3 g of the undecapeptide of Example 23 are added. To the suspension thus obtained are added, at once, 180 ml of TFA. After 20 mins. at ambient temperature, the TFA is evaporated in vacuo at 30° C. The evaporation is stopped when about 60 ml remain in the flask. It is then poured on 500 ml of a 50/50 (volume/volume) mixture of 2-propanol/ether. The solid is drained, washed and dried and 30.5 g of solid are obtained (100%).
CCM/EPAW$_1$ Rf=0.50.

EXAMPLE 25

32.7 g of trifluoroacetate obtained in Example 24 are dissolved in 350 ml of DMF. N-ethylmorpholine (3.8 ml), hydroxybenzotriazol (4.05 g) and 7.44 g of $$\overset{\overset{\text{Acm}}{|}}{\text{Boc—Cys—ONp}}$$

are successively added to the solution. After 45 mins. at ambient temperature, the reaction is completed. The DMF is then evaporated under partial vacuum. The residual volume (about 100 ml) is poured onto a water-ice mixture (600 ml). The precipitate is isolated by draining, then washed with water, methanol (three times) and acetone (three times).

After drying, 32.8 g (93%) are obtained.
CCM/EPAW$_2$ Rf=0.75
BPEW$_1$ Rf=0.65

EXAMPLE 26

$$\overset{\overset{\text{Acm}}{|}\phantom{xx}\overset{\text{Msc}}{|}\phantom{xxxxxxxxxxxxxxx}\overset{\text{Msc}}{|}}{\text{TFA, H—Cys—Lys—Asn—Phe—Phe—Trp—Lys—}}$$

$$\overset{\overset{\text{Acm}}{|}}{\text{Thr—Phe—Thr—Ser—Cys—OPse.}}$$

32.7 g of the dodecapeptide of Example 25 are placed in suspension in the following mixture: dichloromethane 145 ml, ethanedithiol, 17 ml, anisole 8 ml. 170 ml of TFA are then added at once. After 30 mins. at laboratory temperature, the TFA is evaporated in vacuo at 30° C. until a residual volume of 70 ml is obtained which is progressively poured on 700 ml of 2-propanol. The solid is drained, and washed with 2-propanol and ether.

After drying, 33 g (100%) are obtained.
CCM/EPAW$_1$ Rf=0.40.

EXAMPLE 27

$$\overset{\overset{\text{Acm}}{|}\phantom{xx}\overset{\text{Msc}}{|}}{\text{Boc—Ala—Gly—Cys—Lys—Asn—Phe—Phe—Trp—}}$$

$$\overset{\overset{\text{Msc}}{|}\phantom{xxxxxxxxxxxxx}\overset{\text{Acm}}{|}}{\text{Lys—Thr—Phe—Thr—Ser—Cys—OPse.}}$$

33 g of the trifluoroacetate of Example 26 are dissolved in 330 ml of DMF, then 3.6 ml of N-ethylmorpholine, 3.5 g of hydroxybenzotriazol and 7.16 g of Boc—Ala—Gly—OTcp are added. The reaction is completed after 45 mins. at ambient temperature. The DMF is evaporated in vacuo up to a residual volume of about 80 ml. It is poured on the water-ice mixture (600 ml). The solid is drained, washed with water, methanol (three times) and acetone (three times).

After drying, 32 g (93%) are obtained.
CCM/EPAW$_2$ Rf=0.70
BPEW$_1$ Rf=0.60
$[\alpha]_D^{25} = -15°$ (C=1, DMF).

EXAMPLE 28

$$\overset{\overset{\text{Acm}}{|}\phantom{xx}\overset{\text{Msc}}{|}}{\text{TFA, H—Ala—Gly—Cys—Lys—Asn—Phe—Phe—Trp—}}$$

$$\overset{\overset{\text{Msc}}{|}\phantom{xxxxxxxxxxxxx}\overset{\text{Acm}}{|}}{\text{Lys—Thr—Phe—Thr—Ser—Cys—OPse.}}$$

24.7 g of the tetradecapeptide of Example 27 are placed in suspension in 170 ml of dichloromethane to which 20 ml of ethane-dithiol and 10 ml of anisole are added. 200 ml of TFA are added. After 20 mins. at ambient temperature, the TFA is evaporated in vacuo up to a residual volume of about 60 ml. The residue is poured on 2-propanol (600 ml). Draining is effected, followed by washing and drying.

24.8 g of the product (100%) are obtained.
CCM/EPAW$_2$ Rf=0.50.

EXAMPLE 29

Di-Acm-3,14-dihydrosomatostatin 57.5 g of the trifluoroacetate obtained in Example 28 are dissolved in 1 150 ml of DMF. 115 ml of methanol are added. The mixture is placed in an ice bath then, when the temperature is lower than 5° C., the addition of a 0.2 N baryte solution (1 150 ml) is begun. The addition takes place in 40 mins. with a maximum temperature of 15° C. After the end of the addition of baryte, stirring is effected without ice bath until the temperature of $v-18°$ C. is reached. At this moment, a stream of carbon dioxide gas is bubbled in the medium to reach pH 5-6. The barium carbonate is centrifuged. The supernatant matter is evaporated in vacuo at 35°-40° C. up to a residual volume of 600 ml. This residue is poured with stirring in 4000 ml of ethyl acetate: a solid precipitates. Stirring is effected for 1 hr. then draining on fritted glass, washing and drying (in air then in the desiccator).

Yield 42 g (100%) of crude product.

The purification by partition chromatography on a Sephadex G 25 F column or by countercurrent distribution enables a highly pure product to be obtained, titrating more than 98% in HPLC.

The yield is 48%.
CCM/BPEW$_1$ Rf=0.40.

EXAMPLE 30

Dihydrosomatostatin 1.61 g of di-Acm-3,14-dihydrosomatostatin are dissolved in 80 ml of pure AcOH and 72 ml of distilled water (degasified mixture). At laboratory temperature, in the dark, in a nitrogen atmosphere and with stirring, 8.2 ml of 1 N silver nitrate solution are added. Stirring is effected for 16 hrs. The mixture is evaporated to dryness, washed with degasified distilled water. It is taken up in the degasified (60°/40°) DMF/water mixture. A stream of hydrogen sulfide is then passed through, the silver sulfide is centrifuged and the supernatant matter is evaporated to dryness. The residue is dissolved in 50 ml of degasified water, and is lyophilised.

Yield: 1.3 g (86%)

The determination of the product, either by HPLC or by determining the thiol functions, shows a purity of about 70%.

EXAMPLE 31

Somatostatin

The silver salt obtained from 7 g of di-Acm-3,14-dihydrosomatostatin is converted into 3,14-dihydrosomatostatin, according to the technique of Example 30. The solution in the dimethylformamide-water obtained after treatment with hydrogen sulfide, centrifugation and degasification is diluted in 4.6 l of an aqueous solution of 5% acetic acid and added gradually for 18 hrs. to 5.6 l of degasified water containing 12 g of potassium ferricyanide and 24 g of ammonium acetate.

The pH of the medium is maintained for the whole duration of the operation at 6.9 by addition of 8% ammonia solution. This reaction must be effected with stirring and in a permanent atmosphere of inert gas (nitrogen).

After the end of the reaction, the pH of the medium is taken to 5 by addition of acetic acid. The solution is filtered on Biorad AG 3×4 resin in order to eliminate the complex ions, then the product is fixed on a weak acid resin, of the Biorex 70 type. It is washed with a dilute (5%) solution of acetic acid and the product is then eluted with a concentrated (50%) acid solution.

After evaporation of the solution to dryness under a high vacuum and without heating, 5.2 g of a crude reaction product are obtained. The product is purified on a Sephadex G 25 column (H=2000 cm φ 50) using N acetic acid as eluent. After lyophilisation, 2.9 g of a white powdery product are obtained, titrating 98.4% in analytic HPLC.

Yield: 46%; analysis of α-amino acids: suitable.

$[\alpha]_D^{25} = -39°$ (C=1, water) related to the product exempt of water and acetic acid.

CCM/BPEW₁ Rf=0.40.

EXAMPLE 32

N-(o-nitrophenylsulfenyl) L-asparaginyl L-phenylalanyl L-phenylalaninate of methyl.

Nps—Asn—Phe—Phe—OCH₃

80 g of H—Phe—Phe—OCH₃, CF₃COOH are dissolved in 890 ml of DMF containing 23 ml of N-ethylmorpholine. 71.1 g of Nps—Asn—ONSu are then added, and 23 g of hydroxybenzotriazol. The pH is adjusted to 7 by addition of N-ethylmorpholine and stirring is effected overnight at ambient temperature.

Evaporation is effected to dryness until a thick orange oil is obtained. The residue is taken up in ether, the mixture is triturated and a yellow solid is obtained. It is drained and washed with water (twice 900 ml), then methanol (twice 900 ml).

The product is drained, washed with ether and dried in air.

Yield: 88.50 g (82.1%).
CCM/eluent BEW₁ single spot.
$[\alpha]_D^{25} = -33°$ (C=1, DMF).

EXAMPLE 33

N-(o-nitrophenylsulfenyl) L-asparaginyl L-phenylalanyl L-phenylalanine.

Nps—Asn—Phe—Phe—OH

In a flask provided with good stirring means, 139 g of the tripeptide of Example 32 are almost totally dissolved in 1200 m of pyridine, then 253 ml of N sodium hydroxide are added. Stirring is continued for 30 mins. at ambient temperature.

A solid begins to precipitate, 2 430 ml of ether are added to end precipitation. The yellow solid formed is drained, then taken up in 3 800 ml of water and acidified at once with 1 300 ml of glacial acetic acid. The solid obtained is drained, then washed with water and drained. A second washing is effected with methanol.

After draining, the product is dried.

Yield: 127.46 g (94%). CCM/eluent BPEW₂ one spot.

$[\alpha]_D^{25} = -22°$ (C=1, DMF).

EXAMPLE 34

L-asparaginyl L-phenylalanyl L-phenylalanine, hydrochloride

H—Asn—Phe—Phe—OH, HCl

150 g of Nps—Asn—Phe—Phe—OH are dissolved in 1.32 l of DMF. 2.5 equivalents of an HCL gas solution in anhydrous methanol (283 cm3 of 2.28 N solution) are then added, maintaining the temperature at 20° C. The medium is stirred for 30 mins. then evaporated to dryness at 30° C./0.5 mmHg.

The pasty residue is triturated in ethyl acetate until a solid is obtained. The solid is drained and washed several times with ether and dried.

Yield: 118.38 g (98%). CCM/eluent BPEW₁ one spot
$[\alpha]_D^{25} = -9.5°$ (C=1, DMF).

EXAMPLE 35

N-α-tertiobutoxycarbonyl N-ω-methylsulfonylethoxycarbonyl L-lysyl L-asparaginyl L-phenylalanyl L-phenylalanine.

54.72 g of H—Asn—Phe—Phe—OH,HCl are dissolved in 354 ml of DMF containing 59 ml of water. 30 ml of N-ethylmorpholine are added then 63 g of in solution in 236 ml of DMF and 16.15 g of hydroxybenzotriazol. The pH is taken to 7.7 by addition of N-ethylmorpholine and stirring is effected for 2 hrs., the pH being maintained at 7.7.

At the end of these 2 hrs., 6.3 g of

(10% of excess) are added and stirring is continued overnight at ambient temperature. The mixture is evaporated to dryness (30° C./0.5 mmHg), the residue is taken up in 600 ml of water almost saturated in ClNa and 600 ml of ethyl acetate. The pH is taken to 4–4.5 by AcOH, the mixture is decanted and re-extracted with 600 ml of ethyl acetate. The ethyl acetate phases are joined and two volumes of ether are added.

A precipitate is formed which is left for a few hours in the refrigerator. The solid is drained, washed with the minimum of ethyl acetate, then abundantly with ether. The product obtained is then washed with 1.2 l of solution of sulfate-bisulfate of potassium for 30 mins. It is drained, washed well with water, drained and taken up in ether, then drained and dried.

Yield 85 g (95%). CCM/eluent BEW₁ one spot
$[\alpha]_D^{25} = -26.5°$ (C=1, DMF).

EXAMPLE 36

N-ω-methylsulfonylethoxycarbonyl
L-lysyl-L-asparaginyl L-phenylalanyl L-phenylalanine,
trifluoroacetate.

H—Lys—Asn—Phe—Phe—OH, CF$_3$CO$_2$H 82 g of the peptide of Example 35 are dissolved in 400 ml of TFA previously cooled to +5° C. and stirring is continued for 15 mins. at ambient temperature. The insoluble matter is filtered, if necessary.

Evaporation is effected (30° C./0.1 mm) until an oil is obtained. This oil is taken up in 1.6 l of isopropanol and 100 ml of ethyl acetate. An immediate precipitation results.

Draining is effected, followed by washing with ether and drying.

Yield: 76.82 g (92%). CCM/eluent BEW$_1$ one spot
$[\alpha]_D^{25} = -5.1°$ (C—1, DMF).

EXAMPLE 37

N-tertiobutoxycarbonyl S-acetamidomethyl
L-cysteinyl N-ω-methylsulfonyl-ethoxycarbonyl
L-lysyl L-asparaginyl L-phenylalanyl L-phenylalanine.

Boc—Cys—Lys—Asn—Phe—Phe—OH 106 g of the trifluoroacetate of Example 36 are dissolved in 700 ml of DMF containing 116 ml of water and 32.40 ml of N-ethylmorpholine. 54.64 g of Boc—Cys—ONp dissolved in 466 ml of DMF and 18 g of hydroxybenzotriazol are then added. The pH is taken to 7.7 by addition of N-ethylmorpholine and stirring is effected for 2 hrs. at ambient temperature, maintaining the PH at this value.

At the end of these 2 hrs., 5.46 g of

Boc—Cys—ONp(10% of excess)

are added and stirring is continued at ambient temperature overnight. Evaporation is effected to dryness (30° C./0.5 mmHg) and the gel obtained is taken up in 1200 ml of water half saturated with sodium chloride and 1200 ml of ethyl acetate. If the pH is too low, it is taken to 6.5 by N-ethylmorpholine, stirring is effected and the pH is taken to 4–4.5 by the addition of acetic acid.

A precipitate is formed, stirring is effected for 1 hr. in the ice, then the product is left to stand for 1 hr. and draining is effected.

The residue is taken up in a little water, it is triturated, drained, then taken up in 2.4 l of solution of sulfate bisulfate of potassium and stirring is effected for 2 hrs. The product is drained, washed with water, then dried in air. The solid is taken up in the minimum of acetone (700 ml), it is triturated and 4 to 5 volumes of ether are added. The precipitate is drained, washed with ether and dried.

Yield: 123.15 g (96.3%) CCM/eluent BEW$_1$ one spot
$[\alpha]_D^{25} = -28.6°$ (C=1, DMF).

EXAMPLE 38

S-acetamidomethyl L-cysteinyl
N-ω-methylsufonylethoxycarbonyl L-lysyl
L-asparaginyl L-phenylalanyl-L-phenylalanine,
trifluoracetate.

86.44 g of the peptide of Example 37 are added to a mixture of 346 ml of trifluoroacetic acid and 34.6 ml of ethanedithiol previously cooled to 0° C.

The solid dissolves in about 15 mins. and the solution is kept for 15 mins. at ambient temperature with stirring. It is evaporated to dryness (30° C./0.1 mmHg), then is taken up in ethyl acetate and evaporated. This treatment is repeated twice then the mixture is taken up in ether and drained, washed abundantly with ether and dried.

White powder
Yield: 85.96 g (98%). CCM/eluent BEW$_1$ one spot
$[\alpha]_D^{25} = -14.4°$ (C=1, DMF).

EXAMPLE 39

N-tertiobutoxycarbonyl L-alanylglycyl
S-acetamidomethyl L-cysteinyl
N-ω-methylsulfonylethoxycarbonyl L-asparaginyl
L-phenylalanyl L-phenylalanine.

Boc—Ala—Gly—Cys—Lys—Asn—Phe—Phe—OH 119 g of the trifluoroacetate of Example 38 are dissolved in 780 ml of dimethylformamide containing 130 ml of water, then 30.3 ml of N-ethyl morpholine and, immediately, 51.1 g of Boc—Ala—Gly—OTcp in solution in 518 ml of dimethylformamide are added.

16.21 g of dry hydroxybenzotriazol are then added and stirring is continued at ambient temperature for 2 hrs., after having adjusted the pH to 7.7 by N-ethylmorpholine.

5.11 g of solid Boc—Ala—Gly—OTcp are then added. The pH is again adjusted to 7.7 by N-ethylmorpholine and the mixture is left overnight at ambient temperature, with stirring.

Evaporation is effected to dryness (30° C./0.1 mmHg). The oil obtained is taken up in a mixture of 1 liter of ethyl acetate and 1 liter of water almost saturated with sodium chloride. The pH is taken to 5–5.5 by acetic acid and the mixture is left, with vigorous stirring, in an ice bath for 1 hr.

The solid is drained, the cake is washed with a little of the mixture of ethyl acetate-water almost saturated with sodium chloride. The solid is then triturated in the minimum of water, then the solid is drained and stirred for 2 hrs. with a solution buffered at pH 2 (solution of sulfate-bisulfate of potassium). Draining is effected, followed by washing with water and drying overnight in the air. The product is then washed abundantly with ether.

A white powder is obtained.
Yield: 129.1 g (98%) CCM/eluents BPEW$_1$
EPAW$_1$ one spot.
$[\alpha]_D^{25} = -27.3°$ (C=1, DMF).

EXAMPLE 40

```
        Acm  Msc
         |    |
Boc—Ala—Gly—Cys—Lys—Asn—Phe—Phe—Trp—

Msc                        Acm
     |                          |
    Lys—Thr—Phe—Thr—Ser—Cys—OPse
```

75.5 g of the trifluoroacetate of the heptapeptide of Example 15 are dissolved in 1 150 ml of dimethylformamide and 6.3 ml of N-ethylmorpholine are added to the solution. 58.13 g of the heptapeptide of Example 39 are dissolved in 1430 ml of dimethylformamide and 10.81 g of dicyclohexylcarbodiimide and 14.18 g of dry hydroxybenzotriazol are added to this solution.

The first solution is added to the second and the pH is maintained at 7 by addition of N-ethylmorpholine. The mixture is left overnight, with stirring, at ambient temperature.

The reactional mixture is poured in two volumes of ether. The mixture is stirred for 10 mins., then left to stand for 10 mins. at ambient temperature. The precipitate obtained is drained, and washed abundantly in ether.

The solid thus obtained is stirred vigourously for 1 hr. in 1 liter of ether. Draining and drying are effected.

A yellow solid is obtained.

Yield: 100 g (81%).

This product is in all points identical to that obtained in Example 27.

ANALYTICAL CONTROLS

As has been stated hereinabove, the thorough purifications occur only at two stages of the process of synthesis according to the invention, namely the di-Acm-3,14-dihydrosomatostatin and the somatostatin itself.

Consequently, in all the other stages, the analytical controls are limited to chromatographies on a thin layer of silica in various solvent systems, as indicated in the Examples.

On the contrary, for the two stages of thorough purification, the analytical controls are much more important. A method of control by HPLC is added to the conventional methods in peptide chemistry, such as the analysis of amino acids.

The apparatus used is composed of a "Waters Associates" liquid chromatograph: universal injector model U 6 K, pump model 6000 A, multiwavelength detector model 450, Sefram recorder model Servotrace.

The conditions of chromatography are as follows:
Column: column 300×3.9 mm filled with the support μ Bondapak $C_{18}$ 10 μm (Waters Associates)
Elution solvent: the elution solvent is composed of the mixture:
   aqueous solution of $10^{-2}$ M buffered at pH 4 by acetic acid: 700 ml
   acetonitrile for spectroscopy: 250 ml
Rate of flow: 4 ml/min.
Pressure: 210 bars
Detector: UV detector at 210 nm
   sensitivity 0.2 D.O. full scale
Recorder: 10 mV full scale, development 1 cm/min.

Figures 1, 2:
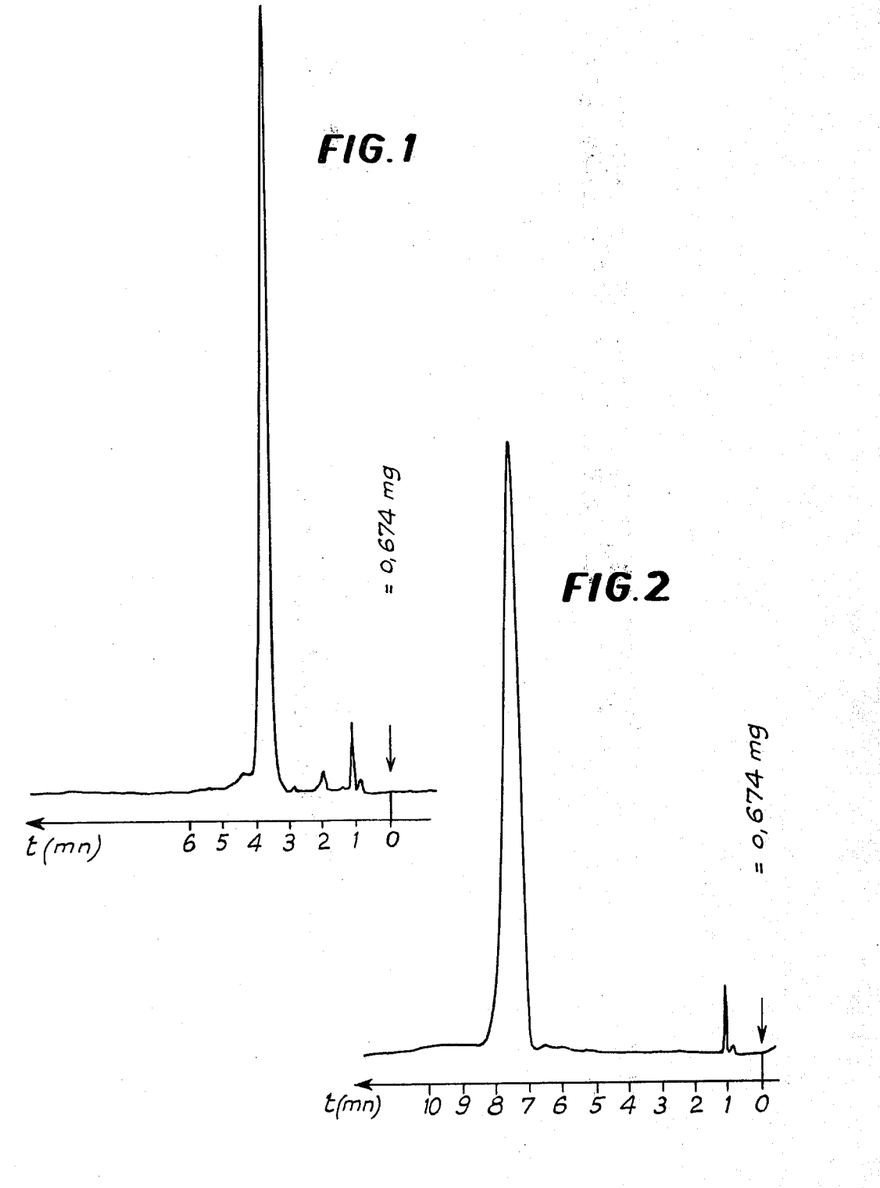

The chromatograms obtained with di-Acm-3,14-dihydrosomatostatin and somatostatin are shown respectively in FIGS. 1 and 2.

They clearly show the uniqueness of the product after the purifications mentioned in the corresponding examples.

What is claimed is:

1. Process for the preparation of somatostatin of formula I:

```
   ┌─────────────────────────────────────────┐
   H—Ala—Gly—Cys—Lys—Asn—Phe—Phe—Trp—
       1   2   3   4   5   6   7   8

┌──────────────────────────────┐
         Lys—Thr—Phe—Thr—Ser—Cys—OH,
          9   10   11   12   13   14
``` by progressive elongation of the peptide chain from the cysteine in 14 position, by successively coupling each aminoacid or peptide whose amino and thiol groups are previously protected, the α-amino group being released and activated in the form of ester before the reaction of formation of the following peptide bond, wherein the acid function of the starting cysteine is protected by the phenylazobenzylsulfonylethyloxy (OPse) group which renders all the intermediate peptides insoluble in water and the usual organic solvents with the exception of dimethylformamide (DMF) and dimethylsufoxide (DMSO) and makes it possible to effect all the peptide coupling reactions in solution in the DMF or DMSO, to precipitate the intermediate peptides by addition of a second solvent and to purify these peptides by washing in solid phase with the aid of suitable solvents which dissolve the impurities.

2. The process of claim 1, wherein the thiol groups of the starting cysteine and the cysteine in 3 position are protected before the coupling reaction by an acetamidomethyl (Acm) group which is conserved up to the last stage of elongation of the peptide chain.

3. The process of one of claim 1 or 2, wherein the first stage consists in preparing the N-t-butoxycarbonyl-S-acetamidomethyl-L-cysteinate of p-phenylazobenzylsulfonylethyl of formula II:

```
       Boc—Cys—OPse
            |
            Acm
``` by condensation of N-t-butoxycarbonyl-S-acetamidomethyl-L-cysteine with p-phenylazobenzylsulfonylethanol in the presence of a dehydrating agent such as dicyclohexylcarbodiimide.

4. The process of claim 1, wherein the ω-amino group of the lysine is protected by a methanesulfonylethyloxycarbonyl (Msc) group before the coupling of this aminoacid in 9 position and in 4 position, group resisting the acid treatments of release of the temporarily protected α-amino groups, and thus being conserved up to the last stage of elongation of the peptide chain.

5. The process of claim 1, wherein the temporary protection of the α-amino groups is ensured by an N-tertiobutoxycarbonyl group (Boc) or by an N-α-biphenylisopropyloxycarbonyl (BPoc) group which is eliminated, before the following coupling reaction, by a strong acid such as trifluoroacetic acid or formic acid with 1% hydrochloric acid.

6. The process of claim 1, wherein the indole nucleus of the L-tryptophane, after introduction of this aminoacid in 8 position, is protected by addition, in the me- dium, of anisole and of thiols such as ethanedithiol or mercaptoethanol.

7. The process of claim 1, wherein the coupling reactions are activated by the addition of hydroxybenzotriazol.

8. The process of claim 1, wherein, after having formed the protected heptapeptide 8 to 14 of formula III:

its coupling is effected directly with the protected heptapeptide 1 to 7 of formula:

previously formed.

9. The process of claim 8, wherein the coupling reaction between the two protected heptapeptides is effected in DMF, in the presence of a coupling agent such as dicyclohexylcarbodiimide or of an activator of the carboxylic function such as the hexafluorophosphate of benzotriazolyloxy (tridimethylamino)phosphonium.

10. The process of either one of claims 8 or 9, wherein the protected heptapeptide 1 to 7 of formula IV hereinabove is prepared from the dipeptide H—Phe—Phe—OCH$_3$, on which is reacted the o-nitrophenolic ester of o-nitrophenylsulfenaminoasparagine in dimethylformamide; after having isolated the protected tripeptide formed, by precipitation by a suitable solvent, all the protector groups are eliminated by a basic treatment then acidolysis and the tripeptide of formula H—Asn—Phe—Phe—OH is used in the terminal free acid form in the following coupling operations, each amino acid being successively brought to react in the form of activated ester and the reactions being effected in the presence of an accelerator such as hydroxybenzotriazol and of a non-racemizing organic base such as N-ethylmorpholine.

11. The process of claim 1, wherein the protected tetradecapeptide obtained, after the last coupling reaction, of formula V:

-continued

Lys—Thr—Phe—Thr—Ser—Cys—OPse (with Msc on Lys, Acm on Cys)

is (a) treated with a strong acid such as trifluoroacetic acid which releases the amine function of the alanine in 1 position, then (b) treated with a strong base such as baryte for 15 to 30 mins. and at ambient temperature, in solution in DMF, this eliminating the protector groups of the side chains of the 2 molecules of lysine and the ester on the cysteine in 14 position, to give di-S-acetamidomethyl-3,14-dihydrosomatostatin which, after purification, is (c) treated in manner known per se to release the thiol functions of the two molecules of cysteine and give the dihydrosomatostatin, which is (d) subjected to final bridging in disulfide between the two cysteine molecules, by a process known per se, to give somatostatin.

12. By way of intermediary necessary in the process of claim 1, N-t-butoxycarbonyl-S-acetamidomethyl-L-cysteinate of p-phenylazobenzylsulfonylethyl of formula II:

13. By way of intermediary necessary in the process of claim 1, the protected heptapeptide 8 to 14 of formula III:

14. By way of intermediary necessary in the process of claim 1, the protected heptapeptide 1 to 7, of formula IV:

15. By way of intermediary necessary in the process of claim 1, the di-Acm-3,14-dihydrosomatostatin of formula VI:

* * * * *